Figure 1:
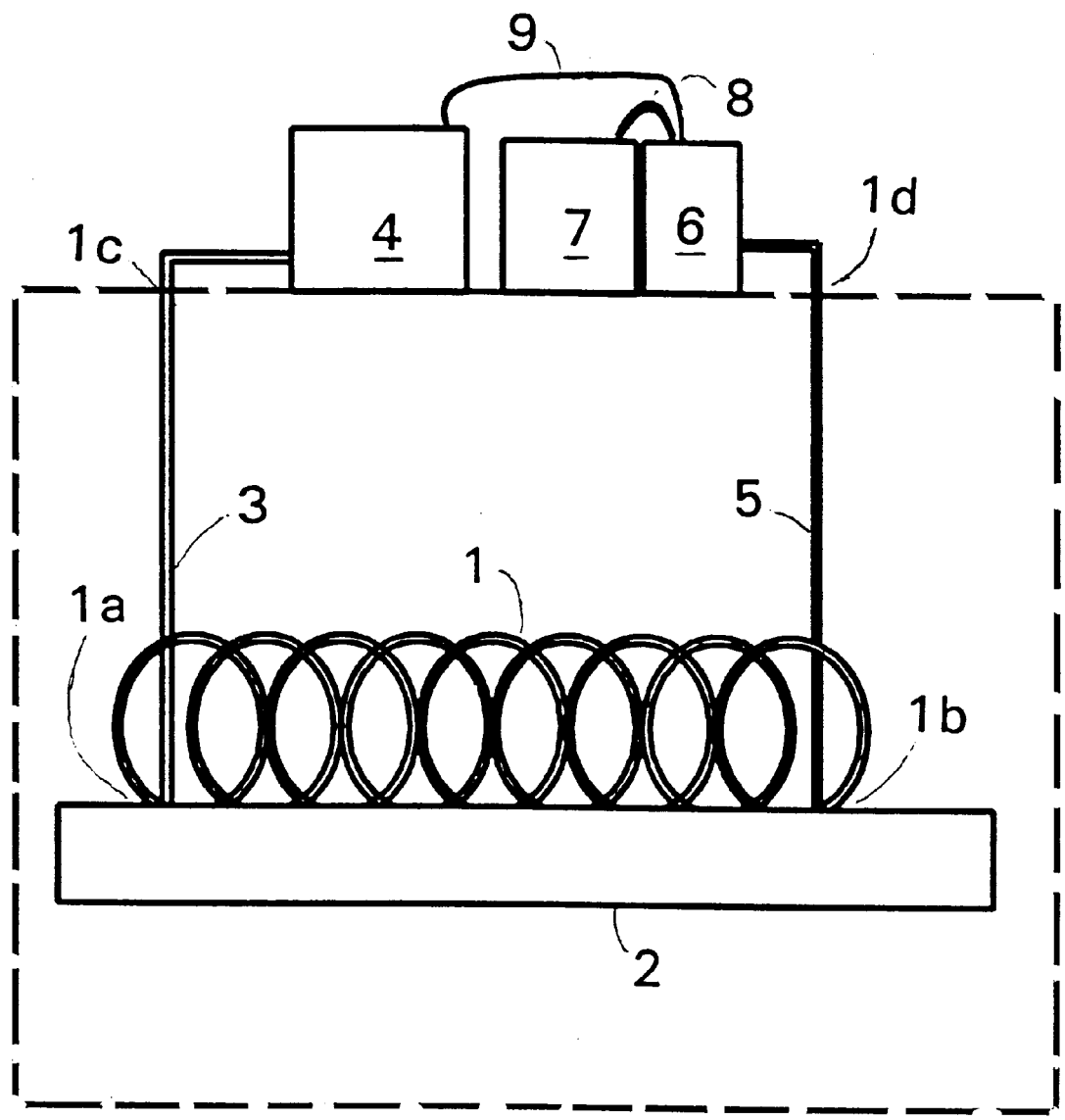

United States Patent [19]
Ahmad et al.

[11] Patent Number: 5,900,556
[45] Date of Patent: May 4, 1999

[54] HELICAL OPTICAL FIBER STRAIN SENSOR

[76] Inventors: Falih H. Ahmad, 9 Ridgeway Pl., Clinton, Miss. 39056; James A. Evans, 607 E. Askew St., Tallulah, La. 71282; Barry D. Fehl, 409 Lake Forest Dr., Vicksburg, Miss. 39180

[21] Appl. No.: 08/929,975

[22] Filed: Sep. 15, 1997

[51] Int. Cl.[6] .................................................... G01L 1/24
[52] U.S. Cl. ........................................ 73/800; 250/227.14
[58] Field of Search ........................ 73/800; 250/227.14, 250/227.16

[56] References Cited

U.S. PATENT DOCUMENTS

| | | |
|---|---|---|
| 4,488,040 | 12/1984 | Rowe ........................................ 250/227 |
| 4,495,411 | 1/1985 | Rashleigh ................................ 250/227 |
| 4,686,631 | 8/1987 | Ruud . |
| 4,717,253 | 1/1988 | Pratt, Jr. .................................... 73/800 |
| 4,725,728 | 2/1988 | Brininstool et al. ...................... 73/800 |
| 4,740,078 | 4/1988 | Daendliker et al. ................... 356/35.5 |
| 4,751,690 | 6/1988 | Krueger ..................................... 73/800 |
| 4,947,693 | 8/1990 | Szuchy et al. ............................ 73/800 |
| 5,381,005 | 1/1995 | Chazelas et al. . |
| 5,381,492 | 1/1995 | Dooley et al. . |
| 5,481,922 | 1/1996 | Washabaugh ............................. 73/800 |
| 5,563,348 | 10/1996 | Suzuki et al. . |

*Primary Examiner*—Max H. Noori
*Attorney, Agent, or Firm*—Luther A. Marsh

[57] ABSTRACT

Strain in concrete is sensed by a helical optical fiber embedded in the concrete and connected at one end to an external light source, and at the other end to a light detector, providing a signal output to an information processor, which provides a display of the strain in the concrete.

5 Claims, 1 Drawing Sheet

HELICAL OPTICAL FIBER STRAIN SENSOR

GOVERNMENT INTEREST STATEMENT

The invention described herein may be manufactured, licensed, and used by or for governmental purposes without the payment of any royalties thereon.

1. BACKGROUND OF THE INVENTION

1. Field of Invention

This invention relates to apparatus and a method of sensing and monitoring strain in concrete structures. More specifically, it relates to a helical optical fiber sensor embedded in concrete, and a method of using the sensor, to monitor the deformation (strain) of concrete due to compression, tension, and bending moment.

2. Description of Prior Art

Strain in concrete structures, such as buildings, foundations, bridges, and dams may cause the failure of such structures, usually with little or no warning. Early detection of strain in concrete structures provides a means of reinforcing or repairing strained regions of concrete before failure occurs. Visual inspection has been found inadequate for monitoring strain in concrete structures. Strain gauges have been used in the past for monitoring strain in concrete structures. They are bonded to the structure, and their electrical resistance changes as strain (deformation) occurs. Optical fiber strain sensors as here disclosed have a higher dynamic range and higher reliability than strain gauges.

Fiber optic sensing means have been disclosed in the prior art. U.S. Pat. No. 5,381,492 discloses a fiber optic vibration sensor having two single-mode optical fibers, one providing a reference signal, and the other one subject to vibrational displacement providing a signal indicative of the perturbation of the sensor. U.S. Pat. No. 5,381,005 describes an optical fiber stress detector, for detecting stresses in structures, using an amplitude-modulated monochromatic light signal that is directed into a reference fiber and a sensing fiber, the phase shift of the sensing fiber output with respect to the reference fiber output being an indication of the stress applied to the detector fiber. This device does not measure strain directly. U.S. Pat. No. 4,686,631 provides an improved method of determining internal stress in polycrystalline solids by X-ray diffraction. U.S. Pat. No. 5,563,348 discloses a stress sensor using changes in the natural frequency of an oscillating string as a means of measuring stress.

2. SUMMARY OF THE INVENTION

The object of this invention is to provide improved means for determining deformation (strain) due to compression, tension, or bending moment in concrete structures such as buildings, foundations, and dams. The strain sensor comprises a helical optical fiber, which is embedded in the concrete, and whose radius is equal to the minimum bending radius (maximum curvature) for the optical fiber material. Light propagating through an optical fiber normally is confined to the interior of the fiber. As the fiber is bent, light remains within the fiber until the radius of curvature reaches a critical value, beyond which light begins to escape from the fiber. This minimum bending radius of a fiber depends upon the properties of the fiber. At least two loops of optical fiber, bent to the minimum bending radius, are normally used. Depending upon the size of the section of structure within which strain is to be monitored, many loops, as many as several hundred, may be used.

The strain sensor further comprises a light source, which directs a light signal into the optical fiber. For example, semiconductor laser light with a wavelength of 1300 nanometers may be used. Light having more than one wavelength, or a continuous spectrum of wavelengths, may also be used. The strain sensor further comprises a light detector which receives the light transmitted through the optical fiber and generates an electrical analog output signal, which may optionally be digitized. This output signal is transmitted by wires to an information processor that analyses the output of the light detector and provides a display indicating the strain of the concrete.

The helical optical fiber typically is made of silicone rubber polymer. It has an inner core, typically with a diameter of 50 microns and an outer layer, or cladding, with a diameter, typically, of 76 microns. The inner core has a refractive index slightly greater than that of the cladding, e.g. 1.465 for the inner core, and 1.460 for the cladding. The loops of the helical fiber are fastened on one side to a preformed housing. The diameter of the loops typically is about 6 cm (radius, 3 cm), and the spacing between turns is about 1 mm. Deformation of the concrete, in which the helical fiber is embedded, cause deformation of the fiber, which alters the transmission of laser light, producing changes in phase of the light, changes in intensity, and in the modes of propagation of the light.

3. BRIEF DESCRIPTION OF THE DRAWING

FIG. 1 is a schematic diagram of the helical optical strain sensor and its ancillary equipment.

4. DETAILED DESCRIPTION OF PREFERRED EMBODIMENT

With reference to FIG. 1, the helical optical fiber 1 is attached along one side of the helix to a preformed housing 2, which holds the loops of the helix in place. The optical fiber typically is made of silicone rubber polymer. It has an inner core typically with a diameter 50 microns and an outer layer, or cladding, typically with a diameter of 76 microns. The inner core has a refractive index slightly greater to than that of the cladding, e.g., 1.465 for the inner core, and 1.460 for the cladding.

The diameter of the loops typically is about 6 cm (radius, 3 cm), and the spacing between turns is about 1 mm. The radius of the helical loops of optical fiber is equal to the minimum bending radius (maximum curvature) for the optical fiber material. Light propagating through an optical fiber normally is confined to the interior of the fiber. Total internal reflection takes place at the sides of the optical fiber. As the fiber is bent, light remains within the fiber until the radius of curvature reaches a critical value, beyond which light begins to escape from the fiber. Bending losses in an optical fiber are a function of the bend radius and the minimum bend radius of the optical fiber. This minimum bending radius of the fiber depends upon the properties of the fiber as described in "Introduction to Optical Fiber Communications Systems," by William B. Jones, Jr., published by Holt, Rinehart and Winston, Inc., 1988, ISBN #0-03-009544-1. A standard procedure by which the minimum bending radius of an optical fiber is measured, is documented in the "Plastic Optical Fiber Data Book," published by MRC Techno Research, Inc., 1993, marketed by Information Gatekeepers, Inc. These two publications are incorporated herein by reference.

At least two loops of optical fiber, bent to the minimum bending radius, are normally used. Depending upon the size of the section of structure within which strain is to be monitored, many loops, as many as several hundred, may be used.

The loops of optical fiber are attached to the preformed housing with an adhesive, typically epoxy glue. The preformed housing may be made of wood, but is a plastic material, such as polyethylene or polyvinylchloride, is normally preferred.

The helical fiber and the preformed housing are embedded in the concrete of the structure whose strain is to be monitored. Accordingly, the helical optical fiber loops and the preformed housing to which they are attached, are placed in the forms before the pouring of concrete. Optical fiber extensions 3 and 5 are placed such that they come to the surface of the concrete. The points of attachment of the optical fiber extensions to the optical fiber are shown at 1a and 1b. The concrete is then poured, vibrated to settle into the cracks and crevices in the form, and allowed to cure. The helical fiber loops and preformed housing are thus embedded in the concrete with the optical fiber extensions 3 and 5 sticking out of the concrete at 1c and 1d, respectively.

The optical fiber extension 3 is connected to an external light source 4, which emits light into the fiber extension 3. The light, typically, is monochromatic, supplied by a laser. For example, semiconductor laser light with a wavelength of 1300 nanometers may be used. However, this invention is not limited to the use of monochromatic light. Several wavelengths, or a continuous spectrum of wavelengths may be used in the optical fiber strain sensor of this invention.

The optical fiber extension 5 is connected to a light detector 6 for receiving light transmitted through the helical fiber 1. The light detector generates a signal indicative of the properties of the light (wavelength, phase, intensity, and modes of propagation). This signal is supplied to an information processor 7 via wires 8 connecting the output of the light detector 6 to the input of the information processor 7. The information processor provides a display of the strain of the concrete at the location where the optical fiber 1 is embedded therein. A wire connection 9 may be provided leading from the light source 4 to the light detector 6 to provide a reference signal that allows the light detector 6 to discern phase shifts between the light entering the optical fiber via optical fiber extension 3, and light exiting from the fiber via optical fiber extension 5. Deformation of the concrete, in which the helical fiber is embedded, causes deformation of the fiber, which alters the transmission of the light, producing phase changes in the light, changes in intensity, and in the modes of propagation of the light. (Modes of propagation of light are reflected in different radial distributions of light intensity across the cross-section of the inner optical fiber.)

It is understood that the above description has been given by way of example only and that other variants may be envisaged.

What is claimed is:

1. An apparatus for sensing strain in concrete structures such as buildings, foundations and dams due to compression and tension (bending moment) comprising:

a. a helical optical fiber embedded in concrete having two ends placed so as to come to the surface of the concrete containing at least two loops bent to the critical bending radius;

b. a light source connected by a first optical extension to one end of the optical fiber for directing a light signal into the optical fiber;

c. a light detector which generates a signal indicative of the properties of the light (wavelength, phase, intensity and modes of propagation) connected by a second fiber extension to the other end of the fiber for detecting the light signal after it has traversed the optical fiber and producing a signal output of the light detector to an information processor whereby the strain of the concrete is computed and displayed by the information processor from the signal output of the light detector.

2. The apparatus in accordance with claim 1 wherein the helical optical fiber is attached along one side thereof to a preformed housing.

3. The apparatus in accordance with claim 1 wherein the critical bending radius of the helical optical fiber consists of an inner core with a diameter of about 50 microns and a refractive index of about 1.465 and an outer layer with a diameter of about 76 microns and a refractive index of about 1.460; said loops having turns and a diameter of about 6 cm (radius, 3 cm) and spacing between turns of about 1 mm embedded in the concrete.

4. The apparatus in accordance with claim 1 wherein the helical optical fiber consists of silicone rubber polymer.

5. The apparatus in accordance with claim 1 wherein the said loops are many depending upon the size of the section of structure within which strain is to be monitored.

* * * * *